US00PP24850P3

(12) United States Plant Patent
Olesen

(10) Patent No.: US PP24,850 P3
(45) Date of Patent: Sep. 9, 2014

(54) MINIATURE ROSE PLANT NAMED 'POULPAH059'

(50) Latin Name: ***Rosa* hybrid**
Varietal Denomination: Poulpah059

(75) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 180 days.

(21) Appl. No.: 13/507,010

(22) Filed: May 31, 2012

(65) Prior Publication Data

US 2013/0326747 P1 Dec. 5, 2013

(51) Int. Cl.
*A01H 5/00* (2006.01)

(52) U.S. Cl.
USPC ..... Plt./116

(58) Field of Classification Search
CPC ..... A01H 5/0222
USPC ..... Plt./117, 116, 118, 119, 121, 124, 125, Plt./144, 145, 122
See application file for complete search history.

*Primary Examiner* — June Hwu

(57) ABSTRACT

A new miniature rose plant that has abundant, near white flowers and attractive foliage. The variety successfully propagates from softwood cuttings and is suitable for year-round production in commercial glasshouses. This new and distinct variety has shown to be uniform and stable in the resulting generations from asexual propagation.

1 Drawing Sheet

Botanical designation: *Rosa* hybrid.
Variety denomination: 'Poulpah059'.

SUMMARY OF THE INVENTION

The present invention constitutes a new and distinct variety of miniature rose plant which originated from a controlled crossing between the female seed parent, an unnamed seedling, and the male pollen parent, also an unnamed seedling.

The two parents were crossed during the summer of 2006 and the resulting seeds were planted in a controlled environment in Fredensborg, Denmark. The new variety, named 'Poulpah059', originated as a single seedling from the stated cross.

The new variety may be distinguished from its male pollen parent and female seed parent primarily by flower coloration and growth habit.

The objective of the hybridization of this rose variety for commercial culture was to create a new and distinct variety with unique qualities, such as:

1. Uniform and abundant near white flowers;
2. Vigorous and compact growth;
3. Year-round flowering under glasshouse conditions;
4. Suitability for production from softwood cuttings in pots;
5. Strong scent;
6. Durable flowers and foliage which make a variety suitable for distribution in the floral industry.

This combination of qualities is not present in previously available commercial cultivars of this type, known to the inventor, and distinguish 'Poulpah059' from all other varieties of which we are aware.

As part of the rose development program, Mogens N. Olesen germinated the seeds from the aforementioned hybridization and conducted evaluations on the resulting seedlings in a controlled environment in Fredensborg, Denmark. 'Poulpah059' was selected by the inventor as a single plant from the progeny of the hybridization in 2006.

Asexual reproduction of 'Poulpah059' by cuttings was first done by Mogens N. Olesen in the nursery in Fredensborg, Denmark in 2007. This initial and other subsequent propagations conducted in controlled environments have demonstrated that the characteristics of 'Poulpah059' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulpah059'. Specifically illustrated in the drawing are flowers at various stages of development, flower in parts, leaves, and stems. Plants photographed are approximately 3 months of age.

DETAILED DESCRIPTION OF THE VARIETY

The following is a description of 'Poulpah059', as observed in its growth in glasshouses in Half Moon Bay, Calif. Observed plants are 3 months of age and were cultivated in 10.5 cm pots. Color references are made using The Royal Horticultural Society (London, England) Colour Chart, 2001, except where common terms of color are used.

For a comparison, several physical characteristics of the rose variety 'Poulhi008', U.S. Plant Pat. No. 15,722. are compared to 'Poulpah059' in Chart 1.

CHART 1

| | 'Poulpah059' | 'Poulhi008' |
|---|---|---|
| Petalage: | 50 petals, 10 of which are petaloids | 40 to 45 petals with 4 to 6 petaloids |
| Petal color as sepals unfold; | Yellow Group 11B with intonatios of Red Group 43C | Red Group 39A |

CHART 1-continued

| | 'Poulpah059' | 'Poulhi008' |
|---|---|---|
| General Tonality of Flower Color: | Orange Group 25A. Flowers become Yellow 11C as they mature. | Red Group 55B. No change in the general tonality at the end of the 6th day. Afterwards, general tonality is Red Group 55C. |

FLOWER AND FLOWER BUD

Blooming habit: Continuous.

Flower bud:

*Size*.—Upon opening, 20 mm in length from base of receptacle to end of bud. 12 mm in diameter.

*Bud form*.—Globose.

*Bud color*.—As sepals unfold, petals are Yellow Group 11B with intonatios of Red Group 43C.

*Sepals*.—Upper Surface: Color: Green Group 139B. Texture: Smooth, weakly pubescent. Lower Surface: Color: Green Group 139B. Texture: Smooth. Shape: Apex: Cirrhose. Base: Flat at union with receptacle. Margins: Margins have strong foliaceous appendages on three of the five sepals. Size: 40 mm long by 25 mm wide.

*Receptacle*.—Surface Texture: Smooth. Shape: Funnel shaped. Size: 5 mm tall and 8 mm wide. Color: Yellow Green Group 144C.

*Pedicel*.—Surface: Smooth. Length: 20 to 25 mm. Diameter: Generally 3 mm. Color: Yellow-Green Group 144C. Strength: Strong.

*Borne*.—Singly, and occasionally up to 3 flowers per branch.

Flower bloom:

*Fragrance*.—Strong, old rose perfume.

*Duration*.—As a pot plant, flowers last up to 21 days.

*Size*.—Flower diameter is 70 to 80 mm when open. Flower depth is 30 mm.

*Form*.—General shape is a hybrid tea with a high pointed center. As the flowers mature, the form becomes a rosette.

*Shape of flower, side view*.—Upon opening, the upper portion is flat. The lower portion is flat. The upper portion becomes a flattened convex as the flower matures.

Petalage: Under normal conditions, flowers have 50 petals total, 10 of which are petaloids.

Color:

*General tonality*.—On open flower Orange Group 25 A. As flowers mature, the coloration becomes Yellow Group 11C.

*Upon opening, petals*.—Outermost and the innermost petals are Orange-White Group 159C on the upper surface. White Group N155C with basal and middle intonations the color of Red-Purple Group 62B on the lower surface. No distinctive coloration at the petal base.

*After opening, petals*.—Outermost and innermost petals are Orange Group 27C with intonations of Orange Group 25D at the middle zone. Basal zone is Yellow Group 10A. Coloration is the same on both upper and lower surface.

Petals:

*Petal reflex*.—Strong.

*Margin*.—Entire with moderate undulations. Weak petal reflex.

*Shape*.—Generally ovate. Apex shape: Rounded. Base shape: Rounded.

*Size*.—35 mm (l) by 45 mm (w).

*Texture*.—Smooth.

*Thickness*.—Average.

Petaloids:

*Quantity*.—10 on average.

*Shape*.—Elliptic. The apex is rounded with a cleft in the margin. Petaloid base is acute.

*Color*.—Same coloration as the petals described above.

*Size*.—20 mm (l) by 12 mm (w).

Reproductive organs:

*Pollen*.—None Observed.

*Anthers*.—Size: 2 mm long. Color: Yellow-Orange Group 21C. Quantity: 40 on average.

*Filaments*.—Color: Yellow-Orange Group 14C. Length: About 3 mm.

*Pistils*.—Length: About 3 mm long. Quantity: 30 on average.

*Stigmas*.—Level relative to the length of the filaments and the height of the anthers. Color: Yellow-Green Group 154C.

*Styles*.—Color: Yellow-Green Group 154C.

*Seed formation*.—Not observed.

PLANT

Plant growth: Upright. Plants are normally 20 cm in height, and 17 cm wide.

Stems:

*Color*.—Juvenile growth: Yellow-Green Group 144A. Mature growth: Yellow-Green Group 144A.

*Length*.—Canes are 10 cm from the base of the plant to the flowering portion.

*Diameter*.—4 mm.

*Internodes*.—On mature canes, there is an average distance of 20 mm between nodes.

*Surface texture*.—Young and mature wood is smooth.

Prickles: Incidence: 8 per 10 cm of stem. Size: Average length is 6 mm. Color: Juvenile and mature prickles are Greyed-Red Group 180C. Shape: Linear.

Plant foliage:

*Compound leaf size*.—80 mm (l) by 65 mm (w).

*Quantity*.—8 leaves per 10 cm of stem.

*Color of juvenile foliage*.—Upper Leaf Surface: Yellow-Green Group 144A. Lower Leaf Surface: Yellow-Green Group 144B. Anthocyanin: Greyed-Purple Group 184C on the upper surface margins and located throughout underneath.

*Color of mature foliage*.—Upper Leaf Surface: Green Group 147A. Lower Leaf Surface: Green Group 147B.

Plant leaves and leaflets:

*Stipules*.—Size: About 7 mm in length. Shape: Linear, slightly broad based with outward extending apices. Margins: Finely serrated with few stipitate glands. Color: Yellow-Green Group 144A.

*Petiole*.—Length: 10 mm on average. Diameter: About 2 mm. Upper surface: Yellow-Green Group 147B. Lower surface: Yellow-Green Group 144B. Surface texture: Smooth.

*Rachis*.—Length: 25 mm on average. Diameter: About 2 mm. Upper surface: Yellow-Green Group 147B. Lower surface: Yellow-Green Group 144B. Surface texture: Smooth.

*Leaflet*.—Number of leaflets: 5 on normal leaves in middle of the stem. Size: 40 mm in length by 25 mm wide. Margin: Serrate. General Shape: Elliptical. Apex Shape: Acute. Base Shape: Round. Texture: Smooth upper and undersurface. Arrangement: Odd pinnate. Venation: Reticulate. Leaf Gloss: Moderately glossy.

Cold hardiness: The variety is tolerant to USDA Cold Hardiness Zone 6.

Heat tolerance: The variety has been found to be suitable for climate conditions found in the American Horticulture Society heat zone 7.

Disease resistance: Average resistance to powdery mildew *Sphaerotheca pannosa,* downy mildew *Peronospora sparsa*, rust *Phragmidium* sps., black spot *Diplocarpon rosae,* and *cinerea* under normal growing conditions.

The invention claimed is:

1. A new and distinct variety of rose plant of the miniature class named 'Poulpah059', substantially as illustrated and described herein, due to its abundant, near white flowers, vigorous growth, compact habit, suitability for production from softwood cuttings in pots, and durable flowers and foliage that make the variety suitable for distribution in the floral industry.

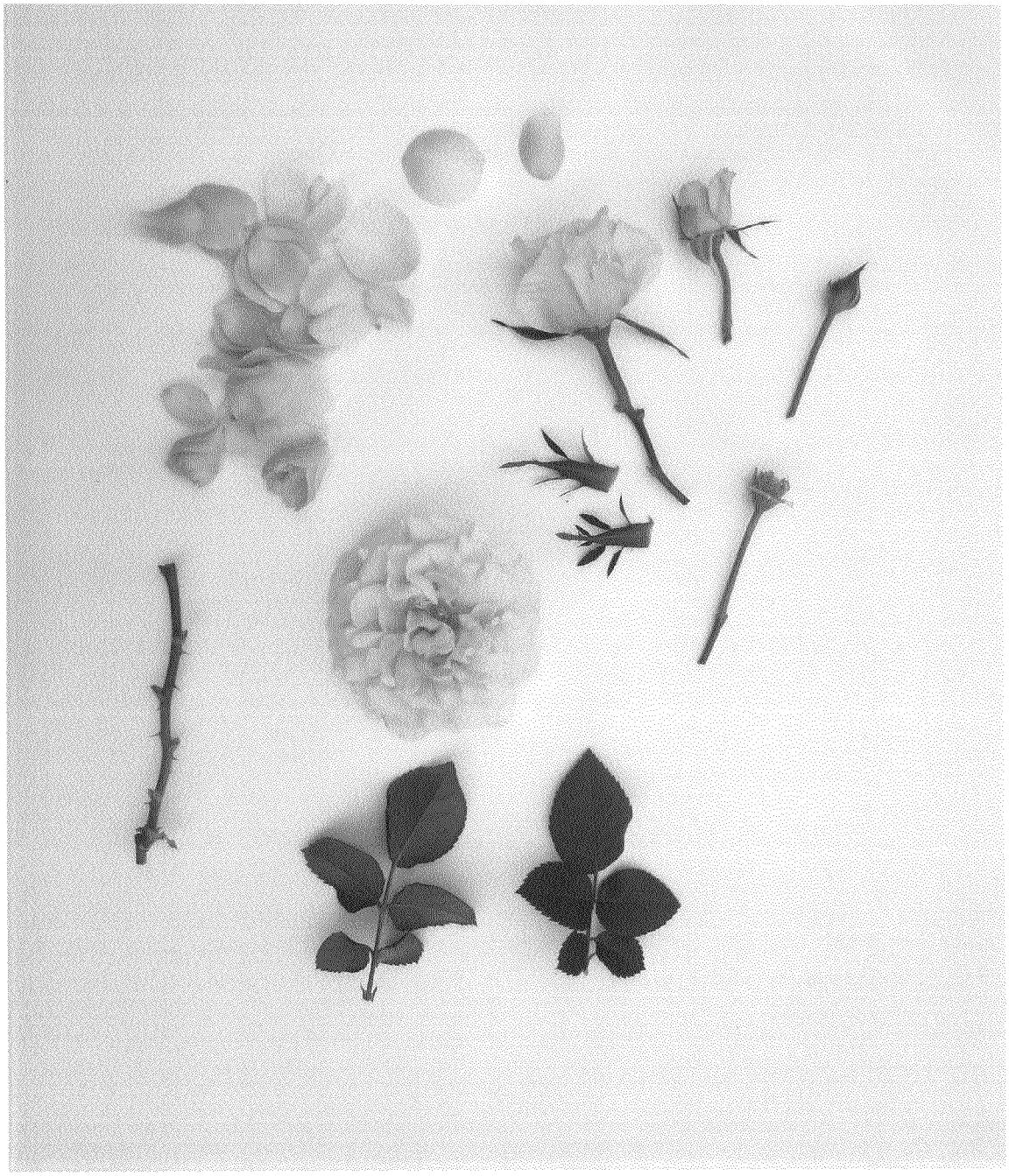

* * * * *